United States Patent [19]
Hegarty et al.

[11] Patent Number: 5,827,433
[45] Date of Patent: Oct. 27, 1998

[54] CONTROL OF OILFIELD BIOFOULING

[75] Inventors: Bryan Martin Hegarty, Peymeinade; Richard Levy, Biot, both of France

[73] Assignee: Rohm and Haas Company, Phila., Pa.

[21] Appl. No.: 542,263

[22] Filed: Oct. 12, 1995

[30] Foreign Application Priority Data

Oct. 12, 1994 [FR] France .................................. 94 12179

[51] Int. Cl.$^6$ .................................. C02F 1/50; C02F 1/76
[52] U.S. Cl. .......................... 210/747; 210/749; 210/753; 210/754; 210/755; 210/764; 422/36
[58] Field of Search .................................. 210/764, 747, 210/755, 749, 753, 754; 422/36

[56] References Cited

FOREIGN PATENT DOCUMENTS 337624  3/1989  European Pat. Off. .

OTHER PUBLICATIONS

Materials Performance, vol. 25, No. 7, Jul. 1986, pp. 39–47, EJ Dewar, Control of Microbiologically Induced Corrosion and Accumulation of Solids in a Sea Water Flood System.

Oil & Gas J., vol. 80, No. 10, Mar. 8, 1982, pp. 253–264, I. Ruseska, J Robbins, JW Costerton & ES Lashen, Biocide Testing Against Corrosion–Causing Oil–Field Bacteria Helps Control Plugging.

Dev. Ind. Microbiol. (J. Ind. Microbiol., Suppl. no. 3), vol. 29, 1988, pp. 247–253, TK Haack, ES Lashen & DE Greenley, The Evaluation of Biocide Efficacy Against Sessile Microorganisms.

*Primary Examiner*—Neil McCarthy
*Attorney, Agent, or Firm*—Julie J. L. Cheng; S. Matthew Cairns

[57] ABSTRACT

The invention describes a process for controlling contamination of oil production system waters by sessile bacteria, comprising a) addition of a slug dose of a biologically effective amount of a quick-kill biocide, simultaneously with or followed by b) intermittent addition of a biologically effective amount of a control biocide.

This dosing regime is found to be surprisingly effective when compared with known dosing regimes.

17 Claims, No Drawings

CONTROL OF OILFIELD BIOFOULING

This invention is concerned with the control of oilfield biofouling in order to increase recovery of oil in water flooding operations. This involves reducing the content and inhibiting the growth and activity of sessile bacteria, especially sulfate reducing bacteria, during the recovery of oil from oil-bearing strata by water flooding.

Water flooding is widely used in the petroleum industry to effect the recovery of oil. This process increases the total yield of oil present in a formation beyond what is usually recovered in the primary process. It is desirable in this process to maintain a high rate of water injection with a minimum expenditure of energy. Any impediment to the free entry of water to oil-bearing formations seriously reduces the efficiency of the recovery operation.

Water flooding systems provide an ideal environment for growth and proliferation of biofilms. Large amounts of water are transported through these systems and injected into oil bearing formations in an effort to maintain reservoir pressure or to increase the mobility of oil through the formation to producing wells. The large surface area of the water distribution network encourages biofouling, which is the attachment and growth of bacteria on the pipe walls.

Biofouling caused by anaerobic bacteria is compounded in water floods by the practice of removing oxygen from the water before injection. The removal of oxygen is done to minimize corrosion of equipment; however, the anoxic conditions provide an ideal environment for the growth of sulfate reducing bacteria (SRB) in the biofilms. This phenomenon is observed both on the injection side and producing side of the water flood operation. The metabolic activity of these bacteria can lead to accelerated corrosion rates, plugging of filters, health hazards from the sulfide production, and eventual souring of the formation (a sour well contains hydrogen sulfide).

A common method used to control biofouling is regular application of a biocide. The biocide is generally selected based on its performance in a standard laboratory evaluation test. Until recently, the test did not address the bacteria in a biofilm, but focused on micro-organisms in the bulk fluid (planktonics). Planktonic organisms are more easily killed than their sessile counterparts because they lack protection afforded by the extra cellular polymeric matrix that is an integral part of the biofilm consortia. Nonetheless, the test is still commonly used because of its convenience.

Glutaraldehyde (pentanedial), which is a highly effective quick-kill biocide, is commonly used to control biofouling, although large amounts are required. If not stored properly, it is unstable on storage. Means for increasing its efficiency have involved admixture with quaternary ammonium halide or phosphonium halide compounds, such as benzyltrimethylammonium halide and the like.

Although isothiazolones, (I, below) may be used as quick-kill biocides their effectiveness is reduced by hydrogen sulfide formed by the existing SRB. Isothiazolones are, however, very effective in preventing the formation of hydrogen sulfide by maintaining a low level of SRB and inhibiting their metabolic activity; in other words, they are very effective control biocides. By "control biocide" in this context is meant any material which is capable of maintaining a low or zero level of microorganism activity in a locus over a period of time. It will be appreciated that most quick-kill biocides also function as control biocides, but that not all control biocides are effective quick-kill biocides—ie effective at rapid killing of microorganisms outright.

EP 337624A discloses a method of reducing sessile SRB which comprises adding periodic slug doses of an alkanedial such as glutaraldehyde as quick-kill biocide, together with a continuous dose of an isothiazolone as control biocide. This was found to be particularly effective compared with other regimes of applying these compounds. If the control biocide is not metered into the system, it is stated that it may be added in small shots. This is in order to provide what is effectively continuous addition in cases where metering is not feasible. Intermittent addition of the control biocide, with defined "on" and "off" periods, or addition at variable concentrations, is not disclosed.

We have now surprisingly discovered that the amount of control biocide applied in such a method can be reduced significantly whilst still maintaining effective bacterial control, leading to potentially substantial cost savings.

Accordingly the present invention provides a process for controlling contamination of oil production system waters by sessile bacteria, comprising
   a) addition of a slug dose of a biologically effective amount of a quick-kill biocide, simultaneously with or followed by
   b) intermittent addition of a biologically effective amount of a control biocide.

By "intermittent addition" is meant that the control biocide is dosed for a certain period of time ("on"), followed by a period of much lower or zero dosing ("off"), this cycle being repeated throughout the treatment. For convenience of operation, the "off" period is generally zero dosing. It is particularly surprising that this regime can be as effective as that in which the control biocide is continuously dosed, as control biocides do not actually kill the bacteria, which are therefore expected to recover once treatment is stopped.

A further aspect of the invention comprises the use of the above process to reduce the amount of control biocide employed in the control of contamination of oil production system waters by sessile bacteria.

The lengths of the "on" and "off" periods can vary considerably. In order for bacterial control to be comparable with that achieved by slug-dosed quick-kill biocide/continuously dosed control biocide, it is preferred that the "off" period is no more than three hours in duration, and preferably no longer than two hours. For practical reasons of operation in the field, the minimum length of the "on" period is preferred to be at least 20 seconds, more preferably at least one minute. Best results have been found when the "on" period is at least 20 minutes, and particularly if it is an hour or longer.

The ratio of "on" to "off" periods can also vary considerably, and indeed it may vary during the course of the treatment, although for convenience it is preferred that the ratio remains constant. Generally the "off" period should be no more than ten times the length of the "on" period, and preferably no more than three times and more preferably no more than twice its length. Best results are obtained when the "on" period is at least the same length as the "off" period, and preferably at least twice as long. In order for some useful cost benefit to be obtained from the process, the "on" period is generally no more than ten times the length of the "off" period, and preferably no more than five times its length.

A typical dosing regime of control biocide is 1 to 3 hours "on" and half an hour to two hours "off", with the "on" period being at least as long as the "off" period.

The slug dose of quick-kill biocide comprises addition of a relatively high concentration of biocide over a period of typically several hours, which is usually repeated at regular but relatively infrequent intervals: generally every one to fifteen days, and typically once a week.

Preferred control biocides are isothiazolones are of the formula:

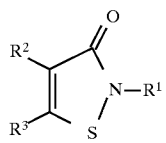

(I)

wherein $R^1$ is $(C_1-C_8)$-alkyl or cycloalkyl; $R^2$ is H or halo and $R^3$ is H or halo. Preferred isothiazolones are 5-chloro-2-methylisothiazolone, or a mixture of 5-chloro-2-methylisothiazolone and 2-methylisothiazolone.

Preferred quick-kill biocides are alkanedials, for example $C_1-C_8$ alkane dials such as propanedial, butanedial, pentanedial, hexanedial and the like. Most preferred is pentanedial (glutaraldehyde). Levels of the quick-kill biocide to be used will vary depending on the degree of biofouling in the system, but amounts from 50 ppm to 1000 ppm will normally be used. Preferred levels are from 100 to 500 ppm, more preferably 150–300 ppm.

Additional substances may be added, such as surfactants, compatible biocides, and the like including quaternary salts, such as quaternary ammonium or phosphonium halide salts, such as organic groups; for example benzyltrialkyl ammonium halides or ADBACs. The preferred level of quaternary is from about 10 to about 50% of the major quick-kill biocide used.

Although other control biocides, such as MBT, DBNPA or metronidazole, acrolein may be added at low levels to be a cleansed system for maintenance of low levels of SRB, isothiazolones, especially the mixture of 5-chloro-2-methyl-4-isothiazolin-3-one and 2-methyl-4-isothiazolin-3-one is particularly efficient and cost-effective, being operable at levels of between 0.1 and 10 ppm, more usually from 0.25 to 5 ppm. Preferred levels are from 0.25 to 2.5 ppm.

It is preferred to add the control biocide in aqueous or aqueous-compatible systems, such as water solution or emulsified dispersion.

If the level of control biocide is insufficient to maintain the SRB content at a low level, a build-up of biofilm and of hydrogen sulfide may occur. The slug dose of quick-kill biocide may be repeated. Even if such should occur, the economics of control are more favourable and the overall clean condition of the water flood system is improved versus the older system of multiple and frequent use of quick-kill biocides.

The preferred combination of alkanedial and isothiazolone is effective in salt or fresh water at any temperature that will support microbial growth. The systems may be static, but in operation, there is motion of water throughout the system. The combination is functional in systems exposed to oxygen, but will generally be used where the oxygen content is reduced for reasons such as corrosion resistance.

EXAMPLES

A biofouling loop designed to simulate the activity of sessile-reducing bacteria was designed to include the following items:

1. an oxygen scrubbing system to provide a source of deionised water into which bisulfite is added;
2. a seawater salt-nutrients concentrate;
3. a source of inoculum for a SRB biofilm;
4. a mixing chamber for 1, 2 and 3;
5. an entry water reservoir for the mixture from 4 and a source of biocide, for supplying;
6. a recirculation system including;
7. a mild steel sampling section.
1. Removal of oxygen from the fluid entering a mild steel device for studying biofilm was required for the rapid establishment of a stable SRB biofilm. Deionized water from a constant supply flowed through three serial nitrogen sparge cylinders. Ammonium bisulfite was metered into the third sparge cylinder. Dissolved oxygen in the deionized water was reduced from 7–9 ppm to <50 ppb by this treatment.
2. A 4× seawater salt-nutrient solution (Table 1) was pumped into the mixing chamber (below) at a rate of 25% of the total fluid flow. The 4× seawater salt-nutrient solution was also sparged with nitrogen.
3. The source of SRB biofilm inoculum was a fixed film reactor (FFR); this concept was adapted from W. G. Characklis's laboratory (8). The FFR was glass vessel packed with sterile granitic rock that was inoculated with a mixed culture of aerobes and SRB from North Sea injection water. A nutrient-containing seawater was pumped through the rockpile at a rate of six liters per day. The effluent from the rockpile was the source of a mixed population of bacteria which could rapidly foul the circulating test loops.
4. The mixer was the source of entry water for each of eight recirculating test loops operating in parallel. Use of a mixer insured that each circulating test loop received an identical entry water feed and greatly reduced the number of pumps and water-carrying lines required for the operation of multiple test loops.
5. The entry water reservoir was constructed of poly(vinyl chloride) (PVC) pipe and fittings. This was the point of water addition to and drainage from each circulating test loop, and was an integral part of the loop. Fluid was pumped into each circulating loop at a rate of 10 ml per minute. An overflow line maintained a constant volume in the recirculating test loops. Each circulating test loop normally contained 300 ml of anaerobic seawater and the fluid retention time was 30 minutes.
6. Circulation in this system was provided by a magnetic drive centrifugal pump. Flow in the mild steel sampling section was normally 1.0 meters per second. Flow rates could be monitored by either a paddlewheel or magnetic flow sensor, and were controlled with a regulating valve. Neoprene tubing was used to connect the components of the circulating test loop to minimize oxygen diffusion into the loops.
7. The mild steel tube sampling section was an 80 cm length of 1.27 cm o.d. seamless mechanical tubing with an 0.08 cm wall.

To sample the biofilm the mild steel tube is wiped with ethanol and a two cm piece cut off with a tubing cutter. This yields a coupon with a 7.0 $cm^2$ sample surface. The inside of the coupon is rinsed with sterile artificial seawater. The biofilm is scraped from the mild steel sample with a sterile microspatula. The biofilm and the coupon are placed in a stoppered tube containing 40 ml of sterile anaerobic artificial seawater and vigorously mixed in a vortex to disperse the biofilm. Viable counts of SRB and aerobes are determined by the most probably number (MPN) technique.

Viable aerobic bacteria counts were determined with a medium containing 20 gm TSB per liter. This medium was a modification of that used in API RP 38. (N-tris [hydroxymethyl]methyl-2-amino-ethanesulfonic acid) was used to buffer the medium in place of phosphate. The medium was supplemented with ammonium, calcium and trace metals. The SRB medium was dispensed anaerobically in disposable Hungate-type tubes (Bellco Glass, Inc.). SRB tubes were incubated for four weeks after inoculation and scored for growth. Experience indicates that the ultimate counts can be determined within this time.

pH was determined with a calomel combination micro electrode. Total sulfide was determined using the methylene blue assay. Dissolved oxygen was measured using CHEMets (CHEMetrics, Inc.).

Glutaraldehyde was added as a 25% aqueous solution. The isothiazolone mixture is a 13.9% aqueous solution of a mixture of the chlorinated and non-chlorinated materials. The mixture is about 3 to 1 of the chlorinated to non-chlorinated.

Example 1

The effect on the activity of sessile SRB of the following dosing regimes was measured:

(1) No biocide added (control).
(2) Slug dose of glutaraldehyde (200 ppm ai) for four hours once a week.
(3) Slug dose of glutaraldehyde as in (1), plus continuous dosing of 1 ppm ai isothiazolone mixture (ie the regime disclosed in EP 337624A).
(4) Slug dose of glutaraldehyde as in (1), plus intermittent dosing of 1 ppm ai isothiazolone mixture comprising 165 minutes dosing ("on") alternating with 75 minutes non-dosing ("off").

Results in Table 1 below are expressed as number of SRB per $cm^2$, and were obtained using the procedure outlined in (7) above. Once treatment has begun, two readings are taken on each measurement day, one before and one after the addition of the slug dose of glutaraldehyde. To permit more convenient comparison of (3) and (4), the percentage of SRB remaining is also given for those two dosing regimes.

TABLE 1

| | | SRB present in mild steel tubing | | | | | |
|---|---|---|---|---|---|---|---|
| Treatment | Days | (1) | (2) | (3) | (3)% | (4) | (4)% |
| None | −21 | $7.30 \times 10^8$ | $7.30 \times 10^8$ | $7.30 \times 10^8$ | 100 | $7.30 \times 10^8$ | 100 |
| None | −14 | $7.30 \times 10^8$ | $7.30 \times 10^8$ | $7.30 \times 10^8$ | 100 | $7.30 \times 10^8$ | 100 |
| None | −7 | $7.30 \times 10^8$ | $7.30 \times 10^9$ | $7.30 \times 10^9$ | 100 | $7.30 \times 10^9$ | 100 |
| Before | 0 | $7.30 \times 10^8$ | $7.30 \times 10^8$ | $7.30 \times 10^8$ | 100 | $7.30 \times 10^8$ | 100 |
| After | | $7.30 \times 10^8$ | 1.00 | 1.00 | <0.1 | 1.00 | <0.1 |
| Before | 14 | $7.30 \times 10^8$ | $7.30 \times 10^8$ | $9.00 \times 10^5$ | 0.12 | $6.39 \times 10^5$ | <0.1 |
| After | | $7.30 \times 10^8$ | $1.46 \times 10^5$ | $9.00 \times 10^2$ | <0.1 | $2.54 \times 10^4$ | <0.1 |
| Before | 21 | $7.30 \times 10^8$ | $3.66 \times 10^8$ | $4.18 \times 10^6$ | 0.57 | $8.87 \times 10^3$ | <0.1 |
| After | | $7.30 \times 10^8$ | $3.13 \times 10^2$ | $1.30 \times 10^2$ | <0.1 | $2.35 \times 10^2$ | <0.1 |
| Before | 28 | $7.30 \times 10^8$ | $6.52 \times 10^8$ | $8.47 \times 10^6$ | 1.2 | $1.02 \times 10^6$ | 0.14 |
| After | | $7.30 \times 10^8$ | $7.17 \times 10^2$ | $6.26 \times 10^2$ | <0.1 | $2.48 \times 10^4$ | <0.1 |
| None | 35 | $7.30 \times 10^8$ | $7.30 \times 10^8$ | $3.94 \times 10^7$ | 5.4 | $2.67 \times 10^7$ | 3.6 |

These results clearly show that intermittent dosing of isothiazolone provides as effective control as continuous dosing. In this case, the amount of isothiazolone employed is reduced by 31%.

Example 2

One of the problems caused by SRB in oilfield systems is their production of hydrogen sulphide gas. Measurement of $H_2S$ production is another way of comparing the efficacy of different biocide dosing regimes. $H_2S$ comes from two sources; there is a small background level from the rockpile bacterial population, and a much greater level produced by the biofilm's SRB population. In Table 2 below, the amount of dissolved sulphide in the circulating seawater was measured daily for the four dosing regimes of Example 1 above. The $H_2S$ levels were measured by a methylene blue spectrophotometric method. Results are quoted in ppm of dissolved sulphide. In (2), (3) and (4), the slug dose of glutaraldehyde was applied at 0, 7 14 and 21 days.

TABLE 2

| | ppm of dissolved sulphide in seawater | | | |
|---|---|---|---|---|
| DAYS | (1) | (2) | (3) | (4) |
| −2 | 1.17 | 1.03 | 0.79 | 1.14 |
| −1 | 1.48 | 1.12 | 1.52 | 1.53 |
| 0 | 0.58 | 0.89 | 0 | 0.36 |
| 1 | 0.77 | 0.31 | 0 | 0 |
| 5 | 2.38 | 0.84 | 0 | 0 |
| 6 | 0.94 | 0.86 | 0 | 0 |
| 7 | 1.10 | 0.89 | 0.13 | 0.11 |
| 8 | 1.68 | 1.12 | 0.14 | 0.12 |
| 9 | 1.53 | 0.41 | 0.15 | 0.10 |
| 12 | 1.10 | 0.27 | 0.31 | 0 |
| 13 | 2.36 | 1.42 | 0 | 0.11 |
| 14 | 2.46 | 0.68 | 0.11 | 0.22 |
| 15 | 2.06 | 0.48 | 0.36 | 0.14 |
| 16 | 2.28 | 0.31 | 0 | 0 |
| 19 | 2.11 | 0.53 | 0.38 | 0.38 |
| 20 | 0.48 | 0.12 | 0.23 | 0.49 |
| 21 | 2.25 | 0.60 | 0.15 | 0.35 |

These results also show that intermittent dosing of isothiazolone in conjunction with slug dosing of glutaraldehyde is as effective at reducing hydrogen sulphide production as continuous dosing.

Example 3

The experiment of Example 2 was repeated using three dosing regimes (ie like regime (4) in Examples 1 and 2). The regimes were 165 mins on, 75 off (the same as regime (4) above); 75 on, 75 off; and 30 on, 60 off; there was also an unpreserved control as in regime (1) above. In Table 3 below, the suffixes B and A after certain days indicate that measurements were taken respectively Before and After application of the slug dose of glutaraldehyde.

TABLE 3

| | ppm of dissolved sulphide in seawater | | | |
|---|---|---|---|---|
| DAYS | 165 ON/ 75 OFF | 75 ON/75 OFF | 30 ON/60 OFF | UNPRESERVED |
| −6.0 | 3.1 | 2.4 | 2.7 | 1.7 |
| −5.0 | 3.0 | 2.4 | 2.8 | 2.1 |
| −4.0 | 3.0 | 2.2 | 2.0 | 2.6 |
| −1.0 | 2.9 | 2.2 | 2.4 | 2.7 |

TABLE 3-continued ppm of dissolved sulphide in seawater

| DAYS | 165 ON/<br>75 OFF | 75 ON/75 OFF | 30 ON/60 OFF | UNPRESERVED |
|---|---|---|---|---|
| 0B | 3.1 | 2.0 | 2.1 | 2.8 |
| 0A | 0.4 | 3.1 | 1.4 | 2.9 |
| 1.0 | 0.2 | 1.5 | 0.0 | 3.2 |
| 2.0 | 1.0 | 0.8 | 0.0 | 2.5 |
| 3.0 | 0.0 | 0.0 | 0.2 | 2.2 |
| 6.0 | 0.0 | 0.4 | 0.0 | 1.8 |
| 7B | 0.1 | 0.3 | 0.2 | 2.1 |
| 7A | 0.3 | 0.2 | 0.2 | 2.1 |
| 8.0 | 0.2 | 0.3 | 0.0 | 1.5 |
| 11.0 | 0.0 | 0.2 | 0.0 | 1.3 |
| 12.0 | 0.1 | 0.1 | 0.0 | 1.6 |
| 13.0 | 0.0 | 0.6 | 0.0 | 1.7 |
| 14 B | 0.0 | 0.0 | 0.0 | 1.6 |
| 14 A | 0.0 | 0.0 | 0.0 | 1.9 |
| 18.0 | 0.0 | 0.0 | 0.0 | 2.2 |
| 19.0 | 0.0 | 0.0 | 0.0 | 2.3 |
| 20 B | 0.0 | 0.1 | 0.1 | 2.2 |
| 20 A | 0.0 | 0.1 | 0.0 | 2.5 |
| 21.0 | 0.1 | 0.2 | 0.2 | 2.2 |
| 22.0 | 0.0 | 0.0 | 0.5 | 2.4 |
| 25.0 | 0.0 | 0.0 | 0.0 | 2.3 |
| 26 B | 0.0 | 0.0 | 0.0 | 2.5 |
| 26 A | 0.0 | 0.0 | 0.0 | 2.8 |
| 27.0 | 0.0 | 0.0 | 0.0 | 2.6 |
| 28.0 | 0.2 | 0.3 | 0.0 | 4.6 |
| 32.0 | 0.8 | 1.2 | 0.0 | 2.7 |
| 33 B | 0.7 | 1.4 | 0.0 | 2.5 |
| 33 A | 0.0 | 0.1 | 0.1 | 3.2 |
| 34.0 | 0.0 | 0.0 | 0.0 | 3.1 |
| 35.0 | 0.0 | 0.8 | 0.0 | 3.6 |
| 36 B | 0.0 | 1.9 | 0.0 | 2.8 |
| 36 A | 0.2 | 0.0 | 0.0 | 2.8 |
| 39.0 | 0.0 | 0.0 | 0.0 | 3.1 |
| 40 B | 0.0 | 0.0 | 0.0 | 3.7 |
| 40 A | 0.0 | 0.6 | 0.0 | 3.6 |
| 41.0 | 0.0 | 0.0 | 0.3 | 3.6 |
| 42.0 | 0.0 | 0.0 | 0.3 | 3.4 |
| 43.0 | 0.0 | 0.2 | 0.3 | 3.3 |
| 46.0 | 0.2 | 0.3 | 0.0 | 3.4 |

The results above show that all three dosing regimes are equally effective.

We claim:

1. Process for controlling contamination of oil production system waters by sessile bacteria, comprising:
   a) addition of a slug dose of a quick-kill biocide in an amount effective to reduce the content and inhibit the growth of sessile bacteria, simultaneous with or followed by
   b) intermittent addition of a control biocide in an amount effective to reduce the content and inhibit the growth of sessile bacteria;
wherein the quick-kill biocide is selected from the group consisting of $(C_1-C_8)$alkanedials and quaternary ammonium or phosphonium halide salts, and the control biocide is selected from the group consisting of methylene-bis-thiocyanate, dibromonitrilopropionamide, metronidazole, acrolein, and isothiazolones.

2. Process according to claim 1, wherein said intermittent addition comprises alternate periods of dosing and zero dosing of the control biocide.

3. Process according to claim 2 wherein the dosing period is at least 20 seconds.

4. Process according to claim 3, wherein the dosing period is at least 20 minutes.

5. Process according to claim 2, wherein the zero dosing period is no more than three hours long.

6. Process according to claim 2, wherein the zero dosing period is no more than ten times the length of the dosing period.

7. Process according to claim 1, wherein the dosing period is at least as long as the zero dosing period.

8. Process according to claim 2, wherein the ratio of duration of dosing to zero dosing period is constant during the intermittent addition.

9. Process according to claim 2, wherein the dosing period is from 1 to 3 hours, and the zero dosing period is from half an hour to two hours, the dosing period being at least as long as the zero dosing period.

10. Process according to claim 1, wherein the slug dose is added periodically during the intermittent addition.

11. Process according to claim 1 wherein the control biocide is an isothiazolone of the formula:

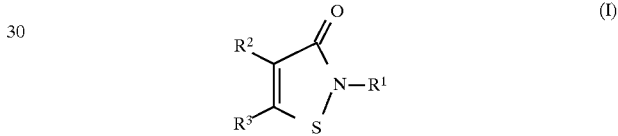

(I)

wherein $R^1$ is $(C_1-C_8)$-alkyl or cycloalkyl; $R^2$ is H or halo and $R^3$ is H or halo.

12. Process according to claim 11 wherein the isothiazolone is 5-chloro-2-methylisothiazolone, or a mixture of 5-chloro-2-methylisothiazolone and 2-methylisothiazolone.

13. Process according to claim 1 wherein the quick-kill biocide is a $(C_1-C_8)$alkanedial.

14. Process according to claim 13, wherein the quick-kill biocide additionally comprises one or more quaternary ammonium or phosphonium halide salts.

15. Process according to claim 1, wherein the quick-kill biocide is dosed at a concentration of from 50 ppm to 1000 ppm.

16. Process according to claim 1, wherein the control biocide is dosed at a level of from 0.1 to 10 ppm.

17. Use of a process according to claim 1 to reduce the amount of control biocide employed in the control of contamination of oil production system waters by sessile bacteria.

* * * * *